US011577948B2

(12) United States Patent
Schoenfelder et al.

(10) Patent No.: US 11,577,948 B2
(45) Date of Patent: Feb. 14, 2023

(54) DEVICE FOR TREATING CONTAINER CLOSURES

(71) Applicant: KRONES AG, Neutraubling (DE)

(72) Inventors: Markus Schoenfelder, Neutraubling (DE); Klaus Buchhauser, Neutraubling (DE); Angela Grünwald, Neutraubling (DE); Sebastian Klepatz, Neutraubling (DE)

(73) Assignee: KRONES AG, Neutraubling (DE)

( * ) Notice: Subject to any disclaimer, the term of this patent is extended or adjusted under 35 U.S.C. 154(b) by 237 days.

(21) Appl. No.: 16/645,280

(22) PCT Filed: Sep. 6, 2018

(86) PCT No.: PCT/EP2018/073936
§ 371 (c)(1),
(2) Date: Mar. 6, 2020

(87) PCT Pub. No.: WO2019/048516
PCT Pub. Date: Mar. 14, 2019

(65) Prior Publication Data
US 2020/0299119 A1 Sep. 24, 2020

(30) Foreign Application Priority Data
Sep. 6, 2017 (DE) .................... 10 2017 120 557.8

(51) Int. Cl.
*B67B 3/00* (2006.01)
*A61L 2/26* (2006.01)
*A61L 2/18* (2006.01)

(52) U.S. Cl.
CPC .............. *B67B 3/003* (2013.01); *A61L 2/186* (2013.01); *A61L 2/26* (2013.01); *A61L 2202/23* (2013.01)

(58) Field of Classification Search
CPC ......... B67B 3/003; A61L 2/186; B65G 29/00; B65G 47/80
(Continued)

(56) References Cited

U.S. PATENT DOCUMENTS 2,873,019 A * 2/1959 Kay ...................... B65G 29/00
198/463.4
3,300,022 A * 1/1967 Sterling .................. B67B 3/061
53/313

(Continued)

FOREIGN PATENT DOCUMENTS

CN 1986378 A 6/2007
CN 101237893 A 8/2008
(Continued)

OTHER PUBLICATIONS

Office Action, Chinese Patent Application 201880071793.2, dated Mar. 15, 2021, 8 pages.
(Continued)

*Primary Examiner* — Robert F Long
*Assistant Examiner* — Xavier A Madison
(74) *Attorney, Agent, or Firm* — Haynes and Boone, LLP

(57) ABSTRACT

A device for treating container closures, for example for disinfecting container closures in a beverage bottling plant, includes a transport disk, rotatable about a vertical rotational axis, for transporting the container closures, and a helical closure guide, arranged above the transport disk, for laterally guiding the container closures, wherein the closure guide has a ceiling guide for guiding the container closures from above.

20 Claims, 6 Drawing Sheets

(58) Field of Classification Search
USPC .......................................................... 53/167
See application file for complete search history.

(56) References Cited

U.S. PATENT DOCUMENTS

| | | | | |
|---|---|---|---|---|
| 3,330,403 | A | * | 7/1967 | Greck ..................... B67B 3/064 |
| | | | | 221/163 |
| 3,960,293 | A | * | 6/1976 | Sweet, II ........... B65G 47/1457 |
| | | | | 221/277 |
| 4,266,653 | A | * | 5/1981 | Mergl ..................... B67C 7/004 |
| | | | | 221/160 |
| 4,958,649 | A | * | 9/1990 | Petho ........................ B08B 3/04 |
| | | | | 198/803.14 |
| 2009/0077930 | A1 | * | 3/2009 | Buchhauser ............ B67B 3/003 |
| | | | | 53/287 |
| 2018/0297789 | A1 | * | 10/2018 | Maibach ............ B65G 47/5136 |

FOREIGN PATENT DOCUMENTS

| | | |
|---|---|---|
| CN | 101401946 A | 4/2009 |
| EP | 0329632 | 8/1989 |
| EP | 2039439 | 3/2009 |
| JP | 1974/116769 | 11/1974 |
| JP | 1990/503998 | 11/1990 |
| JP | H 04100617 | 4/1992 |
| JP | 2001/130516 | 5/2001 |
| WO | WO 2013068379 | 5/2013 |
| WO | WO 2017064186 | 4/2017 |

OTHER PUBLICATIONS

Office Action dated Aug. 4, 2022 in corresponding Japanese patent application No. 2020-513318, 3 pages.

* cited by examiner

DEVICE FOR TREATING CONTAINER CLOSURES

CROSS REFERENCE TO RELATED APPLICATIONS

This application is a national stage of International Application No. PCT/EP2018/073936, filed Sep. 6, 2018, which claims priority from German Patent Application No. 10 2017 120 557.8 filed on Sep. 6, 2017 in the German Patent and Trademark Office, the disclosures of which are incorporated herein by reference in their entirety.

BACKGROUND

Technical Field

The present invention relates to a device for treating container closures, for example for disinfecting container closures in a beverage bottling plant.

Related Art

Devices for treating container closures, for example for disinfecting container closures in a beverage bottling plant, are known.

It is herein known, in aseptic beverage bottling plants, to use dry container closure disinfection systems by means of which the container closures to be placed onto the then filled containers are disinfected. The container closure disinfection systems are provided, for instance, with an inclined channel, along which the container closures to be disinfected slide due to gravitational acceleration and are herein subjected to a disinfectant. This kind of device for disinfecting container closures is of tall construction and therefore requires large hall heights of up to 10 m ceiling height. In order to obtain a necessary throughput of container closures, a multiplicity of container closures must always be guided simultaneously through the channel. On account of the dynamic pressure of the container closures guided through the channel, this can result in a wedging or jamming.

Accordingly, devices are known in which, instead of the conveyance of container closures by way of gravitation, substantially horizontal closure guides are provided, along which the container closures are moved through a disinfection medium by means of a transport device.

From EP 2 039 439 A1, a device for disinfecting container closures, which has a horizontally arranged, helically configured transport path, is known. The container closures are moved from outside to in along the transport path by means of a multiplicity of displacement bodies, wherein each container closure is respectively guided between two displacement bodies. In order to be able to treat various kinds or types of container closures in this device, either the distance between two adjacent displacement bodies has to be respectively adapted to the container closure which is to be newly treated, or else, if a conversion is to be avoided, has to be set to the largest type of container closure. In particular in the conveyance of smaller container closures, this can result, however, in a tilting or wedging of container closures.

JPH04-100617 A shows a device for treating container closures, wherein the container closures are transported from in to out along a horizontally arranged, helically configured transport path by means of an underlying rotating transport disk. The rolling of the container closures along the transport path can result in a tilting and wedging of container closures, whereby the treatment of the container closures has to be interrupted and the blockage cleared.

SUMMARY

An improved device for treating container closures, for example for disinfecting container closures in a beverage bottling plant is described according to various embodiments.

A device for treating container closures, for example for disinfecting container closures in a beverage bottling plant, is proposed, including a transport disk, rotatable about a vertical rotational axis, for transporting the container closures, and a helical closure guide, arranged above the transport disk, for laterally guiding the container closures. The closure guide has a ceiling guide for guiding the container closures from above.

The fact that the closure guide has a ceiling guide for guiding the container closures from above enables the container closures to be constantly held in a position with correct orientation in which an optimal treatment result can be obtained. In particular, a tilting and/or wedging of container closures during transport by means of the transport disk can be avoided. The ceiling guide guides the container closures on that side of the container closures that lies opposite the transport disk. If a container closure transported along the closure guide experiences a tilting moment which would tilt it out of its correctly oriented position, then, as a result of the ceiling guide, a tilting motion of the container closure, resulting from the tilting moment, is limited, or even wholly avoided. In other words, this enables the container closures to be guided both laterally through the closure guide and from above by means of the ceiling guide. Consequently, an enclosure of the container closures from four sides is enabled. Hence only the motional direction along the transport path remains as a movement option for the container closures.

In some embodiments, the closure guide and/or the transport disk and/or the ceiling guide are substantially arranged in such a way that a guidance of the container closures along the predefined guideway is realized.

In various embodiments, a plane which is formed by the thus formed guideway or on which the guideway lies has in relation to the horizontal an inclination in which a downhill force acting in accordance with the angle of inclination on the container closures is sufficiently low that a transport of the container closures by means of the transport disk is not, or only marginally, impaired. In several embodiments, the angle of inclination to the horizontal measures 0° to 5°, for example 0° to 3°. In certain embodiments, the closure guide, the transport disk and/or the ceiling guide are oriented substantially horizontally, so that a guidance of the container closures along a substantially horizontal guideway is realized.

By "vertical" is accordingly understood in the direction of the gravitational acceleration direction, and a deviation from the gravitational acceleration direction in the measure of ±5°, for example ±3°, and in some embodiments without deviation.

In one embodiment, the plane formed by the transport disk is arranged horizontally, and no inclination whatever exists in relation to the horizontal. In other words, the transport disk lies "plumb" and is oriented precisely in the horizontal. With the transport disk, also the closure guide and the ceiling guide is then generally of horizontal construction, so that these are likewise oriented "plumb".

According to another embodiment, the ceiling guide is adjustable in height, for example steplessly adjustable in height. As a result, a distance between the transport disk and the ceiling guide can be adapted to the height of the container closure to be treated, so that the device can be used to treat different kinds of container closures, without this being able to result in a tilting or wedging due to an excessive distance between ceiling guide and container closure. In various embodiments, the height of the ceiling guide is set such that, between the container closures to be conveyed and the ceiling guide, a predefined distance, for example a distance from 1 mm to 10 mm, for example from 2 mm to 8 mm, for example from 4 mm to 6 mm, exists. In other words, the height of the ceiling guide is set such that a vertical distance present between the transport disk and the ceiling guide corresponds to the height of the respective container closure type to be treated, plus the above-stated distance.

By "height-adjustable" is in this sense understood an adjustment in the direction of the vertical rotational axis.

A particularly simple, robust and cost-effective structure can be obtained if the closure guide, according to another embodiment, is fixed.

In order to make it possible for a treatment medium, for example a disinfection medium, for example $H_2O_2$, to be able to reach the container closures during the transport of the container closures, the transport disk, according to another embodiment, is perforated, wherein the transport disk typically has a multiplicity of, generally evenly distributed, perforations.

If the closure guide of another embodiment is accordingly configured such that, in relation to the rotational axis, the container closures are transportable from radially in to radially out, a particularly good treatment result can be obtained. Through the transport of the container closures from radially in to out, the distance from container closure to container closure becomes increasingly large with the relocation of the path in the outward direction, since, with increasing diameter, also the circumference increases. Hence the distance between the individual container closures becomes increasingly large, which helps to prevent a pile-up of container closures.

According to another embodiment, a rotation speed of the transport disk is adjustable, wherein generally, by adjusting the rotation speed of the transport disk, a dwell time of a container closure to be treated is adjustable. It is thereby enabled that the container closures to be treated always dwell in the device for a necessary period and can be subjected to the treatment, for example the disinfection. Moreover, a clock rate with which the container closures reach the end of the closure guide can thereby be adjusted.

According to another embodiment, a housing, for example a sealed housing, houses the transport disk, the closure guide and the ceiling guide. As a result, inside the housing can be provided a treatment chamber, in which a climate necessary for the treatment of the container closures or a desired climate can be purposefully adjusted. Generally, a treatment medium, such as a disinfection medium, for example $H_2O_2$, is conducted into the interior of the housing.

According to another embodiment, a closure feed for feeding container closures onto the transport disk, for example a clocked closure feed for the clocked feeding of the container closures, is provided. It is thereby possible to feed container closures in a purposeful manner to the transport disk.

In various embodiments, an outlet for the removal of container closures from the transport disk, for example a clocked outlet for the clocked feed-out of the container closures, is provided. It is thereby possible to remove container closures from the transport disk in a purposeful manner.

In accordance with several embodiments, a plurality of outlets for the removal of container closures from the transport disk is provided, wherein generally each of the outlets is provided for a specific container closure type. The device can hence be used to treat different container closure types, wherein, because a plurality of outlets are provided, a system including the device can be configured such that a conversion is necessary only in the device. In particular, in cleanroom systems or aseptic systems, a violation of the cleanroom atmosphere in a capper chamber in which filled containers are capped with the container closures can here be spared.

Hence, in accordance with each outlet, a downstream transport device assigned to the respective container closure type can be provided—for instance a transport rail—by means of which the container closures are then conveyed to the following treatment facility—for instance the capper.

According to some embodiments, a discharge device for feeding the container closures from the closure guide to the at least one outlet is provided between the closure guide and the at least one outlet.

In order to enable an uncomplicated conversion of the device from the treatment of one closure type to another closure type, the discharge device, according to another embodiment, can have an exchangeable insert, wherein generally inserts of different shape are insertable into the discharge device, wherein each insert is configured to feed the container closures to a specific outlet. Typically, each of the outlets is provided for one or more specific container closure types. Depending on which container closure type is due to be treated, an appropriate insert is used, that the container closures are respectively fed to the outlet provided for the discharge of the respective container type.

If the discharge device, in accordance with another embodiment, has an adjustable switch element, wherein the switch element is adjustable between a plurality of switch positions, the switch element, in each of the switch positions, feeding the container closures to a different outlet, the device can be easily converted from the treatment of container closures of one type to the treatment of container closures of another type. The conversion can here in particular be realized by a simple adjustment of the switch, for example in consequence of a control command. An intrusion into or opening of the housing of the device is hence not necessary.

In order to be able to discharge contaminants from the device, according to a further embodiment a drain can be arranged on a bottom region of the housing, wherein the drain is generally arranged in the region of an outlet and the drain is typically configured such that particles and/or liquids to be drained off can be drained into an isolator adjoining the device. In several embodiments, the drain is configured together with an outlet for delivering the container closures from the device to a treatment device downstream of the device, for example to a capper for capping containers with the container closures, or a transport device for transporting the container closures to the capping device. Hence, as a result, no separate outlet has to be provided, furthermore the materials to be removed can be led off into the chamber housing the further treatment device.

According to certain embodiments, a surge opening for the admission of a flushing medium, and/or a gas inlet for the admission of a treatment medium, for example a treatment gas, for example $H_2O_2$, and/or a gas outlet for the removal of the treatment medium, for example treatment gas, for example $H_2O_2$, is/are provided. A flushing of the device or a stream of treatment medium can thereby be obtained.

In order to obtain a particularly secure guidance of the container closures through the closure guide and/or the ceiling guide, the closure guide and/or the ceiling guide, in accordance with a further embodiment, can have a continuous, for example one-piece, strip material, for example a sheet-metal strip.

The throughput or output of the device can be easily increased if, according to another embodiment, a plurality of closure guides is provided, wherein generally each closure guide has a separately height-adjustable ceiling guide.

BRIEF DESCRIPTION OF THE FIGURES

Further embodiments of the invention are explained in greater detail by the following description of the figures.

DETAILED DESCRIPTION

Illustrative embodiments are described on the basis of the figures. Same, similar or like-acting elements in the different figures are here provided with identical reference symbols, and a repeated description of these elements is partially dispensed with in order to avoid redundancies.

Figure 1:
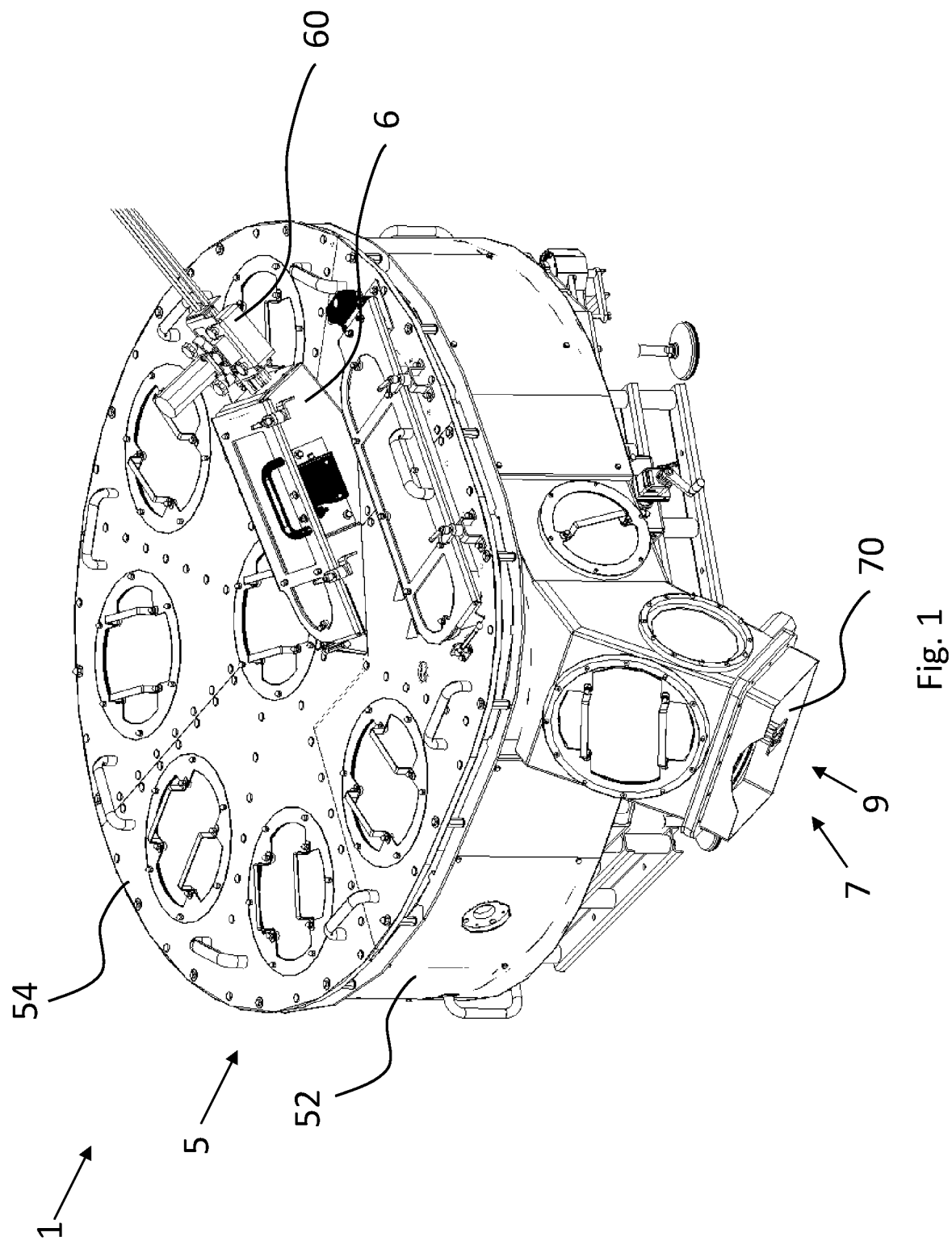
FIG. 1 shows schematically a perspective side view of a device for treating container closures according to a first embodiment.

In FIG. 1, a perspective side view of a device 1 for treating container closures according to a first embodiment is shown schematically. The device 1 has a sealed housing 5, which includes a base (not shown), a side wall 52 and a removable cover plate 54. For the feeding of container closures to be treated into the device 1, a clocked closure feed 6 is arranged on the cover plate 54. The closure feed 6 receives via a closure slide 62, from a closure sorting device (not shown) upstream of the device 1, sorted container closures to be treated. The closure feed 6 has a lock 60, by means of which the container closures to be treated can be individually planted.

In the housing 5 is also arranged an outlet opening 70, in which an outlet 7 for the removal of treated container closures from the device 1 is arranged. In a beverage bottling plant, the outlet opening 70 or the outlet 7 can be sealingly connected to a further transport device (not shown), which feeds the treated container closures to a container capper.

The outlet opening 70 of the outlet 7 extends partially over a bottom region of the housing 5, wherein the outlet opening 70 is further provided as a drain 9 for draining from the housing 5 particles and/or liquids to be drained. The particles and/or liquids to be drained can thereby be drained off into an isolator adjoining the device 1.

Figure 2:
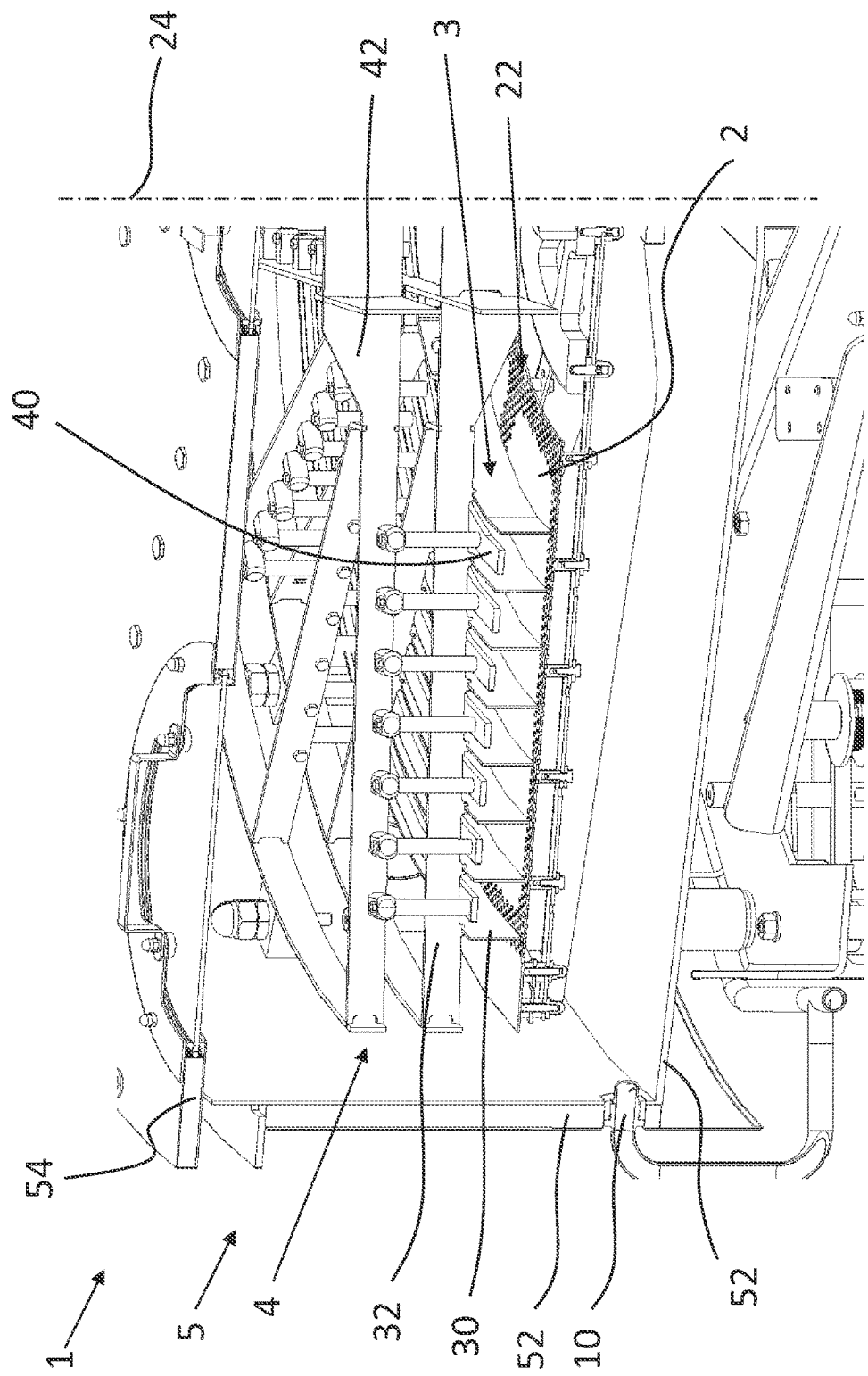
FIG. 2 shows schematically a perspective sectional detailed view of the device from FIG. 1.

FIG. 2 shows schematically a perspective sectional detailed view of the device 1 from FIG. 1. The housing 5 houses a transport disk 2, rotatable about a vertical rotational axis 24, for transporting the container closures, and a helical closure guide 3, arranged above the transport disk 2, for laterally guiding the container closures. The closure guide 3 has a continuous, helical sheet-metal strip 30, for example of one-piece configuration, which is fixedly arranged on a plurality of beams 32. Beneath the helical sheet-metal strip 30 is arranged the transport disk 2, which has a multiplicity of evenly distributed perforations 22.

In addition, a height-adjustable ceiling guide 4 for guiding the container closures from above is provided. The ceiling guide 4 has a helically configured, flat guide plate 40, which is fastened to a mounting 42 that is adjustable in height in the direction of the rotational axis 24. By displacement of the mounting 42 in the direction of the rotational axis 24, a distance present between the guide plate 40 and the transport disk 2 is altered.

For the treatment of the container closures to be treated, the transport disk 2 is set in rotation. Container closures to be treated are fed via the closure feed 6 (see FIG. 1), into an initial region of the closure guide 3 close to the rotational axis 24, onto the transport disk 2. As a result of the rotary motion of the transport disk 2, the container closures present on the transport disk 2 experience a rolling on the closure guide 3 along a guideway defined by the shape of the closure guide 3. The container closures hence experience, in relation to the rotational axis 24, a transport from radially in to radially out. As a result of the transport of the container closures from radially in to out, the distance from container closure to container closure becomes increasingly large with the outward relocation of the path, since, with increasing diameter, also the circumference increases. The distance between the individual container closures hence becomes increasingly large, which helps to prevent a pile-up of container closures.

The ceiling guide 4 is arranged such that the guide plate 40 extends between the sheet-metal strip 30. The ceiling guide 4 enables the container closures to be constantly held in a position with correct orientation, in which an optimal treatment result can be obtained. In particular, a tilting and/or wedging of container closures can be avoided. The ceiling guide 4 here guides the container closures on that side of the container closures that lies opposite the transport disk. If a container closure transported along the closure guide 3 experiences a tilting moment which would tilt it out of its correctly oriented position, then, by virtue of the ceiling guide 4, a tilting motion of the container closure, resulting from the tilting moment, is avoided. The container closures are hence guided both laterally through the closure guide 3 and from above by means of the ceiling guide 4.

Through the perforations 22 of the transport disk 2, contaminants fall from the transport disk 2 onto the underlying base 52 of the housing 5. Close to the base 52, in the side wall 54 is arranged a surge opening 10 for the admission of a flushing medium. By the admitted flushing medium, the base 52 is flushed and the contaminants, for instance particles and/or liquids, are flushed out in the direction of and through the drain 9 (see FIG. 1). In order to ensure an advantageous drainage, the base 52 is slightly inclined, in the present case by about 3°, in the direction of the drain 9. The base 52 hence has no vertical faces on which water or cleaning agent can remain. As a result, the drying time of the device 1 after a cleaning can also be kept short.

In the housing 5 are further provided a multiplicity of gas inlets (not shown) for the admission of a treatment gas, in the present case $H_2O_2$, and a multiplicity of gas outlets (not shown), for the removal of the treatment gas, in the present case $H_2O_2$. Through the provision of the gas inlets and gas outlets, a treatment gas stream through the interior of the housing can be generated, whereupon the container closures present on the transport disk 2 come into contact with the treatment gas stream and are thereby disinfected. The basic structure of the gas inlets and gas outlets is known per se and can be gleaned, for instance, from EP 2 039 439 A1.

In an alternative embodiment, only one gas inlet, for example in the region of the middle of the housings 5, is provided. The gas inlet can be provided, for instance, in the vicinity of the closure feed 6.

One or more gas outlets can be provided in the region of the outlets 7, 7', 7".

The rotation speed of the transport disk 2 is adjustable, so that a dwell time of the container closures 11 to be treated is adjustable.

Figure 3:
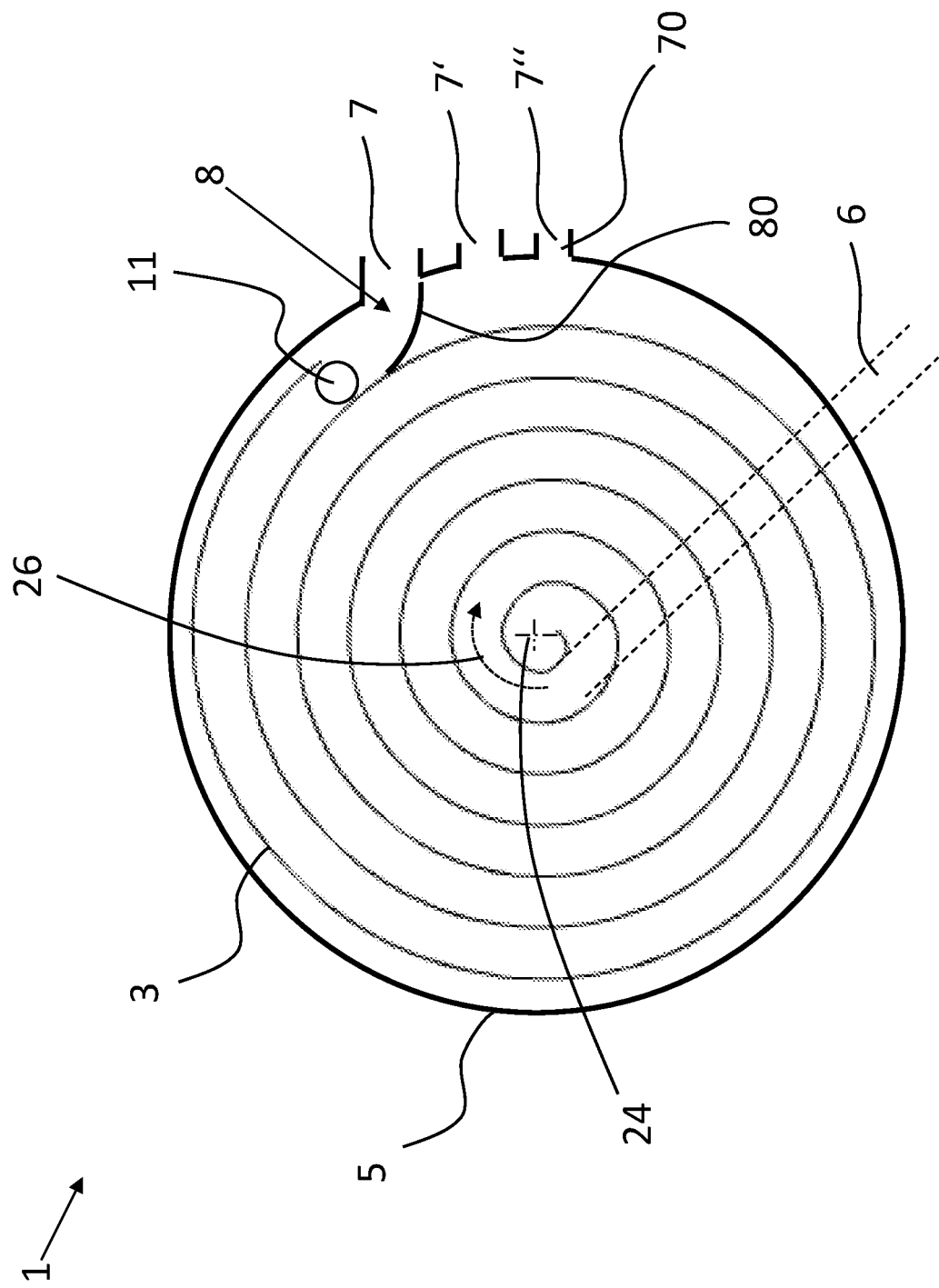
FIG. 3 shows schematically a sectional view of the device from FIG. 1.

FIG. 3 reveals in schematic representation a sectional view of the device 1 from FIG. 1. As already described above, the closure feed 6 guides the container closures 11 to be treated into a middle region of the closure guide 3. As a result of the rotary motion, here indicated with the reference symbol 26, of the transport disk 2 (not shown) about the rotational axis 24, the container closures 11 are moved along the helical closure guide 3, in relation to the rotational axis 24, from radially in to radially out, whereupon they come into contact, during transport, with the treatment gas. They then make their way to a discharge device 8, which is arranged between the closure guide 3 and a plurality of outlets 7, 7', 7" for the feed-out of the container closures 11 from the transport disk 2 and out of the housing 5. Each of the outlets 7, 7', 7" is here provided for the discharge of container closures of a specific container type.

In an exemplary embodiment, the discharge device 8 can also provide a clocked release of the container closures.

The discharge device 8 has in the present case a first insert 80, which is configured to feed container closures 11 of a first type to a first outlet 7. The insert 80 is configured such that it is exchangeable. If the device 1 is to be converted in order to treat container closures 11 of a different type, this insert can be removed and replaced by a different insert.

Figure 4:
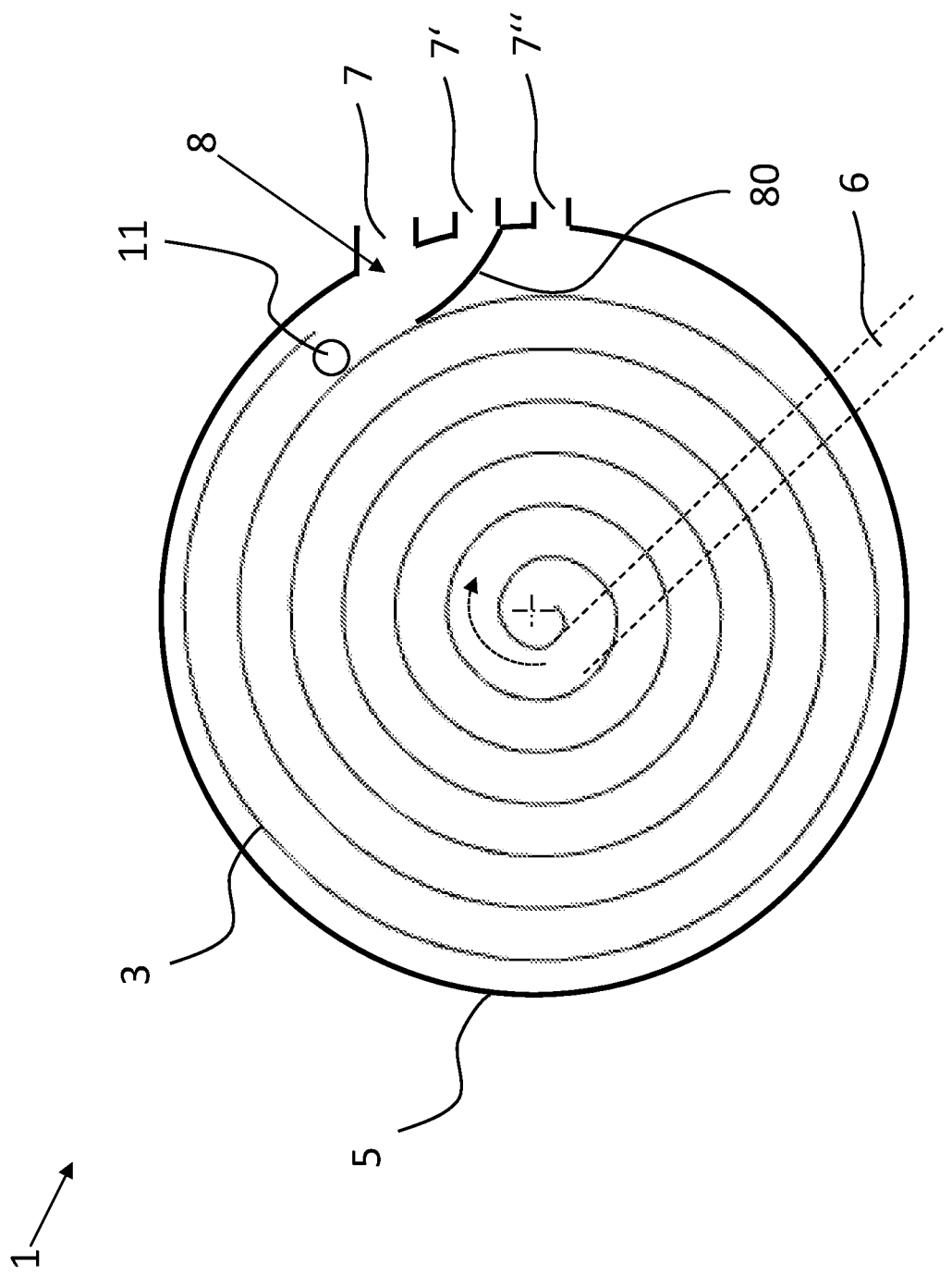
FIG. 4 shows schematically a further sectional view of the device from FIG. 1.

In FIG. 4, the device 1 from FIG. 1 is shown schematically in a sectional view following conversion for the treatment of container closures 11 of a second type. In place of the first insert 80, the discharge device 8 now has a second insert 80', which, in terms of its position in the device 1 and its shape, is different from the first insert 80. The second insert 80' is hence configured to feed container closures 11 of a second type to a second outlet 7'.

Figure 5:
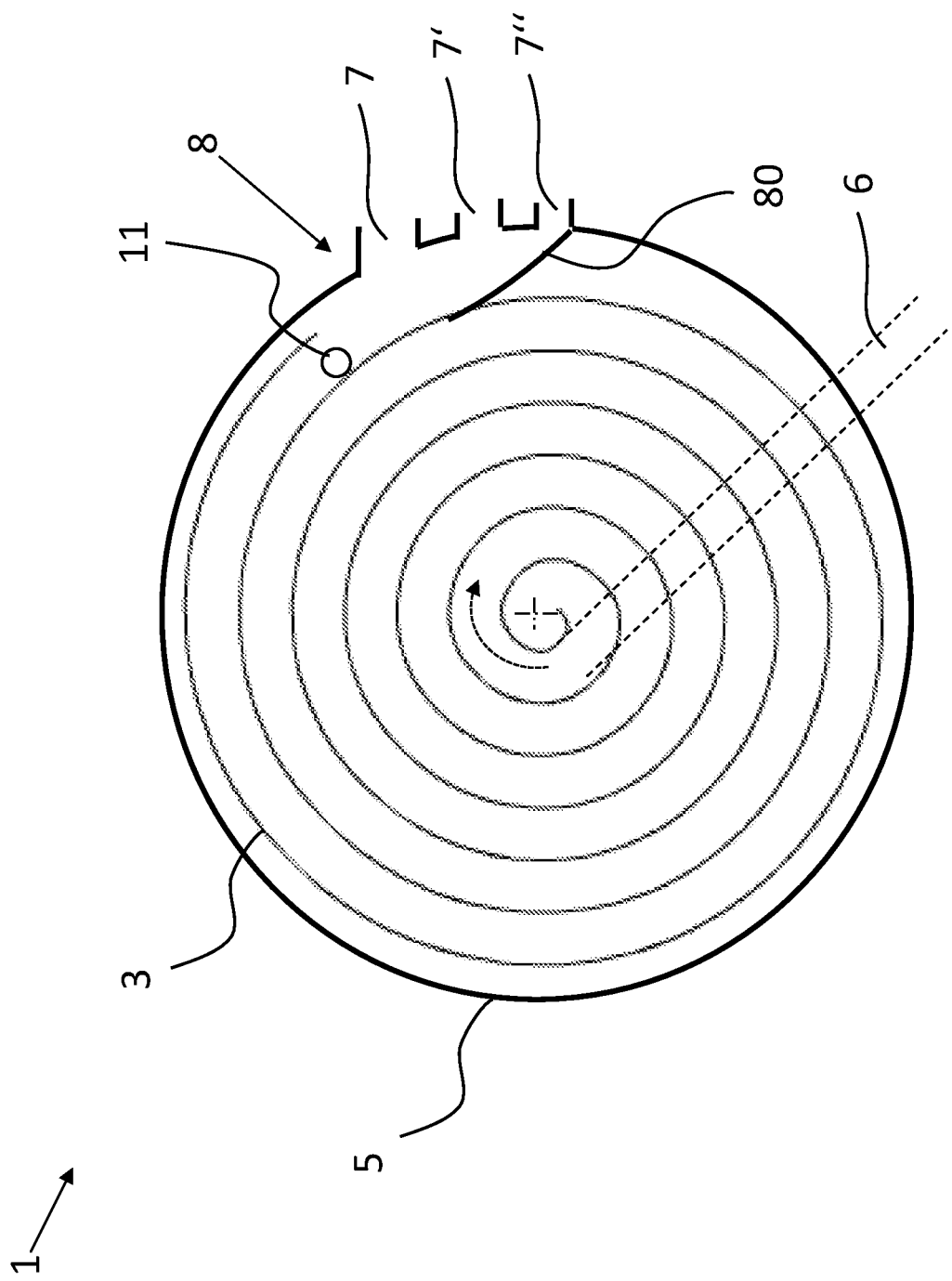
FIG. 5 shows schematically a further sectional view of the device from FIG. 1.

In FIG. 5, the device 1 from FIG. 1 is shown schematically in a sectional view following renewed conversion for the treatment of container closures 11 of a third type. In place of the first or second insert 80, 80', the discharge device 8 now has a third insert 80", which, in terms of its position in the device 1 and its shape, is different from the first and second insert 80, 80'. The third insert 80" is hence configured to feed container closures 11 of a third type to a third outlet 7".

Figure 6:
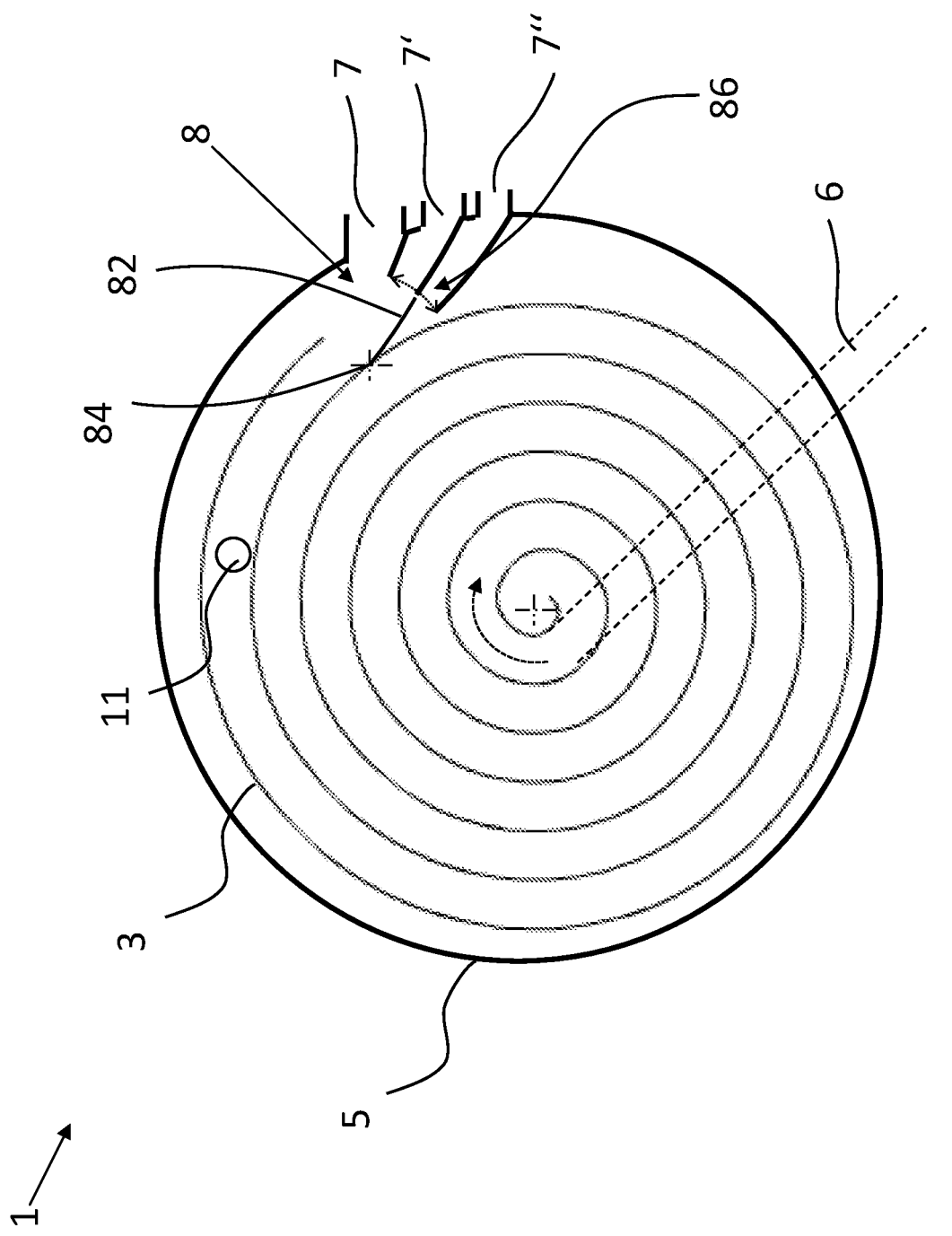
FIG. 6 shows schematically a sectional view of a device for treating container closures according to a further embodiment.

In FIG. 6, a sectional view of a device 1 for treating container closures 11 is shown schematically according to a further embodiment. In terms of its structure, the device 1 substantially corresponds to the device 1 from FIGS. 1 to 5, wherein the device 1 according to the illustrative embodiment shown in FIG. 6 has a discharge device 8 which, instead of different, exchangeable inserts, has an adjustable switch element 82, wherein the switch element 82 is pivotable about a pivot axis 84, within a pivot range 86, between a plurality of switch positions, wherein the switch element 82, in each of the switch positions, feeds the container closures 11 respectively to a different outlet 7, 7', 7". In FIG. 6, the switch 82 is shown positioned in a second switch position, so that the container closures 11 are fed to the second outlet 7'. In order to convert the device for the treatment of container closures 11 of a different type, the switch 82 has merely to be set to a different switch position. Opening of the housing 5 in order to exchange two inserts is not necessary.

Where applicable, all individual features which are represented in the illustrative embodiments can be mutually combined and/or exchanged without departing from the scope of the invention.

The invention claimed is:

1. A device for treating container closures in a beverage bottling plant, which comprises:
   a transport disk configured to be rotatable about a vertical rotational axis and to transport the container closures; and
   a helical closure guide arranged above the transport disk, the helical closure guide configured to laterally guide the container closures,
   wherein the helical closure guide comprises a ceiling guide configured to guide the container closures on a side of the container closures that lies opposite the transport disk and the ceiling guide comprises a helically configured, flat guide plate that is fastened to a mounting that is adjustable in height in a direction of the vertical rotational axis.

2. The device of claim 1, wherein the transport disk is perforated.

3. The device of claim 1, wherein the helical closure guide is further configured such that, in relation to the vertical rotational axis, the container closures are transportable from radially in to radially out.

4. The device of claim 1, wherein a rotation speed of the transport disk is adjustable.

5. The device of claim 1, further comprising a housing configured to house the transport disk, the helical closure guide, and the ceiling guide.

6. The device of claim 5, further comprising a drain arranged on a bottom region of the housing, the drain configured to drain off particles or liquids into an isolator adjoining the device.

7. The device of claim 1, further comprising:
   a closure feed configured to feed the container closures onto the transport disk; and
   an outlet configured to remove the container closures from the transport disk.

8. The device of claim 7, wherein:
   the closure feed comprises a clocked closure feed; or
   the outlet comprises a clocked outlet.

9. The device of claim 1, further comprising a plurality of outlets configured to remove the container closures from the transport disk, wherein each of the plurality of outlets is configured to remove a specific type of container closure.

10. The device of claim 9, further comprising a discharge device configured to feed the container closures from the helical closure guide to at least one outlet from the plurality of outlets, wherein the discharge device is disposed between the helical closure guide and the at least one outlet.

11. The device of claim 10, wherein the discharge device comprises an exchangeable insert configured to feed the container closures to a specific outlet from the plurality of outlets.

12. The device of claim 11, wherein the exchangeable insert comprises a plurality of exchangeable inserts, each insert having a different shape.

13. The device of claim 10, wherein the discharge device comprises an adjustable switch element, wherein the adjustable switch element is configured to be adjustable between a plurality of switch positions, and the adjustable switch element, in each of the switch positions, feeds the container closures to a different outlet from the plurality of outlets.

14. The device of claim 1, further comprising:
a surge opening configured to receive a flushing medium;
a gas inlet configured to receive a treatment gas; or
a gas outlet configured to remove a treatment gas.

15. The device of claim 1, wherein the helical closure guide or the ceiling guide comprises a continuous strip material.

16. A device for treating container closures in a beverage bottling plant, which comprises:
a transport disk configured to be rotatable about a vertical rotational axis and to transport the container closures; and
a plurality of helical closure guides arranged above the transport disk, the plurality of helical closure guides configured to laterally guide the container closures,
wherein each helical closure guide comprises a separate height-adjustable ceiling guide, each height-adjustable ceiling guide is configured to guide the container closures on a side of the container closures that lies opposite the transport disk, and each height-adjustable ceiling guide comprises a helically configured, flat guide plate that is fastened to a mounting that is adjustable in height in a direction of the vertical rotational axis.

17. The device of claim 16, further comprising:
a closure feed configured to feed the container closures onto the transport disk; and
a plurality of outlets configured to remove the container closures from the transport disk, wherein each of the plurality of outlets is configured to remove a specific type of container closure.

18. The device of claim 17, further comprising a discharge device configured to feed the container closures from the helical closure guide to at least one outlet from the plurality of outlets, wherein the discharge device is disposed between the helical closure guide and the at least one outlet.

19. The device of claim 18, wherein the discharge device comprises an exchangeable insert configured to feed the container closures to a specific outlet from the plurality of outlets, and wherein the exchangeable insert comprises a plurality of exchangeable inserts, each insert having a different shape.

20. A device for treating container closures in a beverage bottling plant, which comprises:
a transport disk configured to be rotatable about a vertical rotational axis and to transport the container closures;
a helical closure guide arranged above the transport disk, the helical closure guide configured to laterally guide the container closures, wherein the helical closure guide comprises a ceiling guide configured to guide the container closures on a side of the container closures that lies opposite the transport disk; and
a plurality of outlets configured to remove the container closures from the transport disk, wherein each of the plurality of outlets is configured to remove a specific type of container closure.

* * * * *